US008958060B2

(12) United States Patent
Chen

(10) Patent No.: US 8,958,060 B2
(45) Date of Patent: Feb. 17, 2015

(54) OPTICAL FIBER MECHANICAL BEND STRESS TEST SYSTEM WITH OPTICAL TIME-DOMAIN REFLECTOMETER

(71) Applicant: Verizon Patent and Licensing, Inc., Basking Ridge, NJ (US)

(72) Inventor: David Zhi Chen, Richardson, TX (US)

(73) Assignee: Verizon Patent and Licensing Inc., Basking Ridge, NJ (US)

(*) Notice: Subject to any disclaimer, the term of this patent is extended or adjusted under 35 U.S.C. 154(b) by 9 days.

(21) Appl. No.: 13/772,593

(22) Filed: Feb. 21, 2013

(65) Prior Publication Data

US 2014/0233019 A1 Aug. 21, 2014

(51) Int. Cl.
*G01N 21/00* (2006.01)
*H04B 10/08* (2006.01)
*H04B 17/00* (2006.01)
*G01N 21/17* (2006.01)

(52) U.S. Cl.
CPC ..................................... *G01N 21/17* (2013.01)
USPC ............................................ 356/73.1; 398/21

(58) Field of Classification Search
None
See application file for complete search history.

(56) References Cited

U.S. PATENT DOCUMENTS

| | | | |
|---|---|---|---|
| 6,850,318 B1* | 2/2005 | Ito et al. | 356/73.1 |
| 8,027,584 B2* | 9/2011 | Healey | 398/16 |
| 8,531,655 B2* | 9/2013 | Klein et al. | 356/73.1 |
| 2009/0207409 A1* | 8/2009 | Yao | 356/365 |
| 2011/0149293 A1* | 6/2011 | Dorner | 356/460 |
| 2012/0224168 A1* | 9/2012 | Hirai et al. | 356/73.1 |

OTHER PUBLICATIONS

David Boivin ; Louis-Anne de Montmorillon ; Lionel Provost ; Nelly Montaigne ; Frans Gooijer ; Eugen Aldea ; Jaap Jensma ; Pierre Sillard; Recent developments in bend-insensitive and ultra-bend-insensitive fibers. Proc. SPIE 7598, Optical Components and Materials VII, 75980G (Feb. 25, 2010).*

* cited by examiner

*Primary Examiner* — Tri Ton
*Assistant Examiner* — Willie Merrell, II

(57) ABSTRACT

Methods and devices provide for storing historical data that includes interference values mapped to at least one of bend radii values, lifetime values, or failure rate values of optical fibers; transmitting an optical signal, via a test system, toward the optical fiber under test; setting a polarization state of the optical signal before the optical signal propagates through the optical fiber under test; setting a polarization state of a reflected optical signal that has propagated through the optical fiber under test in a manner that causes a minimum interference or a maximum interference; measuring instances of power of the reflected optical signal; and outputting a result that includes at least one of a bend radius value, a lifetime value, or a failure rate that applies to the optical fiber under test based on the measured instances of power and the historical data.

20 Claims, 12 Drawing Sheets

OPTICAL FIBER MECHANICAL BEND STRESS TEST SYSTEM WITH OPTICAL TIME-DOMAIN REFLECTOMETER

BACKGROUND

Passive optical components are tested for its performance and reliability requirements in accordance with various national and international standards.

DETAILED DESCRIPTION OF PREFERRED EMBODIMENTS

Figure 1:
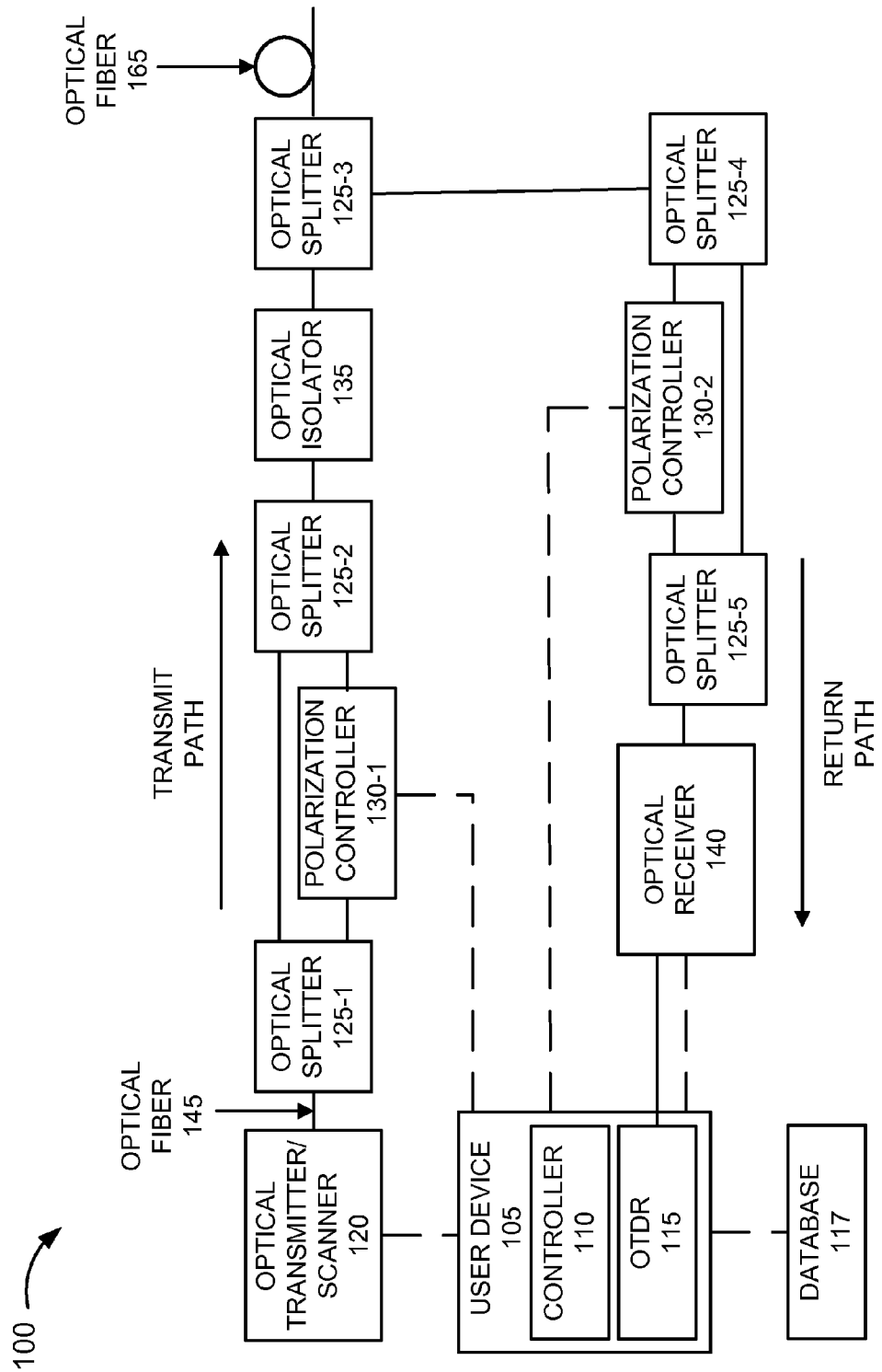
FIG. 1 is a diagram illustrating an exemplary embodiment of a test system capable of testing an optical fiber under test to estimate a bend radius, a lifetime, a failure rate, or some combination thereof.

The following detailed description refers to the accompanying drawings. The same reference numbers in different drawings may identify the same or similar elements. Also, the following detailed description does not limit the invention.

Previously in the industry, installers pulled a fiber drop cable through a micro-duct. According to this approach, tight bend mechanical stress points in the optical fiber were not an issue. Thereafter, in the industry, installers began using the ultra bend insensitive fiber (UBIF G.657.B3). By limiting the drop cable diameter to at least 4.8 mm, this provided another way to control the tight bend radius to >=5.0 mm without using the micro-duct. Currently in the industry, installers may use a 0.9 mm (900 μm) fiber drop cable directly. Thus, there is a potential risk to bend the drop cable, for example, within the <5 mm radius limitation. This may occur even when an installer pulls the small diameter drop through a sharp corner without using a corner bend limiter or the installer neglects to install a corner protector.

A bend in an optical fiber (e.g., a bend-insensitive fiber (BIF, G.657.A2/B2) or an ultra-bend insensitive fiber (UBIF, G.657.B3)) having a certain bend radius may reduce the lifetime of the optical fiber, may eventually cause a break in the optical fiber, or a combination thereof. In view of this fact, a bend close to its physical-material limitation, such as a tight bend, in an optical glass-fiber should be detected. The term "tight bend," as used herein refers to the mechanical bending limitation. The bend radius associated with a tight bend may (slightly) differ depending on the optical fiber and its optical fiber characteristics (e.g., fiber coating, brand, tight buffer, materials used, thickness, etc.). By way of example, a bend radius of a tight bend may range from 7.5 mm-10 mm or may be less than 5 mm. However, the ability to detect mechanical stress points or bends for these types of optical fibers (e.g., BIF, UBIF) can be difficult because there may be no measurable signal loss (e.g., insertion loss, return loss, etc.).

An optical fiber that is not subjected to high mechanical stress (e.g., a tight bend) does not exhibit distinctive birefringence. In general, the bend radius around 10~30 mm is not an issue. However, if the bend radius reaches (e.g., 5 mm or below), it can cause extreme mechanical stress in the optical fiber. Additionally, when there is mechanical stress in the optical fiber, this condition can cause visible and detectable birefringence.

According to an exemplary embodiment, a test system is capable of detecting a location of a tight bend in an optical fiber under test based on a measurement of degree of interference and time data. According to an exemplary embodiment, the test system generates an optical signal and transmits the optical signal along a transmit path toward the optical fiber under test. According to an exemplary implementation, the test system includes a polarization controller to set the polarization state of the optical signal to two orthogonal modes. When the optical signal goes through the optical fiber under test having a tight bend, the optical signal will change (e.g., a change in polarization) due to birefringence and the mechanical stress associated with the tight bend.

According to an exemplary implementation, the test system includes a polarization controller to align or de-align the polarization state of a reflected optical signal to allow for a measurement of a minimum interference, a maximum interference, or a combination thereof. According to an exemplary implementation, the test system includes an optical time-domain reflectometer (OTDR). The test system uses time data, associated with reflected optical signals that are caused by a tight bend and mechanical birefringence, and the measured degree of interference(s), to detect the location of the tight bend in the optical fiber under test.

According to an exemplary embodiment, the test system is capable of correlating the interference to a bend radius of the optical fiber. According to an exemplary embodiment, the test system is capable of correlating the bend radius to a lifetime of the optical fiber. According to an exemplary implementation, the test system uses historical data to perform correlations. For example, the test system includes or has access to a database, a data structure, or other suitable architecture that stores historical data. The historical data may include data from different sources. For example, the historical data may include data from a research and development team associated with the development of the same type of optical fiber, as the optical fiber under test, during the pre-manufacturing stage. Additionally or alternatively, the historical data may include data from the manufacturer of the same type of optical fiber. Additionally, or alternatively, the historical data may include data from installers in the field relating to the same type of optical fiber.

The historical data may also include data based on theoretical calculations. For example, the mechanical breaking point and sustainable time before an optical fiber breaks under different environmental conditions may be derived from theoretical calculations. The theoretical calculations may be based on the structure of a glass material under stress and the forces (e.g., tension force, compression force, etc.) associated with a tight bend.

According to an exemplary embodiment, the historical data includes a mapping between measurements of interference to bend radius. Additionally, according to an exemplary embodiment, the historical data includes a mapping between bend radius and lifetime of an optical fiber. According to another exemplary embodiment, the historical data includes a mapping between measurements of interference and lifetime of an optical fiber. As described further below, the historical data may include data pertaining to the optical fiber (e.g., material of optical fiber, type of optical fiber (e.g., UBIF, BIF), category (e.g., G.657.B3, etc.)) and the optical signal (e.g., wavelength, power, etc.) used to generate the historical data. The historical data may include other factor, such as environmental conditions (e.g., temperature, humidity, above ground, in-ground, etc.), the number of bends in the optical fiber, a distance between bends, measurements of bend radii, etc.

As previously described, the test system uses historical data to perform correlations. For example, in the case of correlating a measurement of interference to a certain bend radius, the historical data from the research and development team, the manufacturer, or a combination thereof, may include data that maps an interference value (or range of interface values) to a bend radius (or a range of bend radii). For example, a maximum interference value may be mapped to a bend radius, a minimum interference value may be mapped to a bend radius, or some other interference value between maximum and minimum values may be mapped to a bend radius.

The test system may be implemented in a lab or a testbed setting (e.g., for developmental testing, characterizations, certifications, etc.). According to such an implementation, the historical data may be generated based on a series of tests using the test system. The tester may enter various data, such as optical fiber data, bend radii values, optical signal data, interference values, etc., as described further below.

Alternatively, the test system may be implemented in the field. For example, an installer of an optical fiber in a building (e.g., a multi-dwelling unit, a residential home, etc.) may use the test system to identify a tight bend in the optical fiber and determine whether to reconfigure a bend radius based on a predicted lifetime of and/or a failure rate for the optical fiber under test. Additionally, depending on the experiences of the installer with respect to the optical fiber, the installer may update or add historical data. For example, assume that the installer performs a test and the historical data indicates that, despite the bend, the optical fiber has a lifetime of 20 years. The following week, the installer is called to repair the optical fiber because of breakage. Under these circumstances, the installer may update the historical data.

The optical fiber under test may be a bend-insensitive fiber or an ultra-bend insensitive fiber. The optical fiber may be a single mode fiber, but multimode fiber can also be used by properly setting the interference requirements.

FIG. 1 is a diagram illustrating an exemplary embodiment of a test system 100. Test system 100 is capable of locating a tight bend in an optical fiber under test. Test system 100 is also capable of generating test data pertaining to the measurement of interference of an optical signal that propagated through the optical fiber under test and correlating this measurement to a bend radius of the optical fiber under test, a lifetime of the optical fiber under test, or a combination thereof.

As illustrated, test system 100 includes a user device 105. User device 105 includes a controller 110 and an optical time-domain reflectometer (OTDR) 115. User device 105 may include a database 117. Alternatively, user device 105 may be communicatively coupled to a database 117 (e.g., via a network (not illustrated), etc.). Test system 100 further includes an optical transmitter/wavelength scanner 120, optical splitters 125-1 through 125-5 (also referred to generally as optical splitter 125), polarization controllers 130-1 and 130-2 (also referred to generally as polarization controller 130), an optical isolator 135, and an optical receiver 140. Test system 100 includes optical fiber 145 to connect optical components to one another. As further illustrated in FIG. 1, an optical fiber 165 (i.e., a device under test) is connected to test system 100.

The number of components and the configuration of test system 100 are exemplary. According to other embodiments, test system 100 may include additional components, fewer components, different components, and/or differently arranged components, than those illustrated in FIG. 1. For example, test system 100 may include an optical filter, an optical attenuator and/or optical amplifier. That is, depending on the capabilities of optical transmitter/wavelength scanner 120 to provide levels of granularity of wavelength and/or power (e.g., fineness or coarseness), the optical filter, the optical attenuator, and/or the optical amplifier may be added to test system 100. Additionally, test system 100 may be implemented having a different order of components along an optical signal path than the order of components illustrated in FIG. 1.

The connections between the components of test system 100 are exemplary. According to an exemplary embodiment, user device 105 is communicatively coupled other components (e.g., optical transmitter/scanner 120, polarization controllers 130) of test system 100, as indicated by the dashed lines depicted in FIG. 1, for control purposes and/or to receive/transmit data.

User device 105 includes a computational device. For example, user device 105 may be implemented as a computer. For example, the computer may be a desktop computer, a laptop computer, or a handheld computer. According to an exemplary embodiment, user device 105 includes a controller 110. Controller 110 may be implemented as software. Controller 110 provides user interfaces to allow a user to control other components of test system 100 and to conduct tests. For example, the user may configure various test parameters, control the operation of test system 100, obtain and analyze test data pertaining to tests that are conducted, and provide test results to the user.

Optical time-domain reflectometer 115 stores time values pertaining to optical signals transmitted by optical transmitter/wavelength scanner 120 and receipt of reflected optical signals by optical receiver 140. Optical time-domain reflectometer 115 is used to calculate a location of a tight bend in the optical fiber under test (i.e., optical fiber 165) based on time values associated with an optical signal (e.g., launch time, receiver time) and the time values associated with measured degrees of interferences of the optical signal reflected from the tight bend and mechanically stressed locations, as such interference instances occur over time. As described further below, polarization controller 130 sets the polarization of the reflected optical signal in a manner that produces degrees of interference that may be identified at optical receiver 140. User device 105 is described further below.

Database 117 includes a storage device that stores historical data. The historical data may include mappings between measurements of the degree of interferences to tight bend radii and their related mechanical stresses and mappings between tight bend radii and lifetimes of optical fibers. Alternatively, the historical data may include mappings between measurements of the degree of interferences and lifetimes of optical fibers. According to an exemplary implementation, the measurements of interferences include maximum interference, minimum interference, interference levels between maximum and minimum, or some combination thereof.

The historical data includes data pertaining to a mapping. For example, a mapping between a maximum interference and a tight bend radius relates to a particular type of optical fiber, optical signal, and other factors, as described further below. For example, historical data includes data pertaining to the optical fiber. The optical fiber data may include data pertaining to the material of the optical fiber, the material thickness of the optical fiber (which is related to the fiber index profile design, such as single trenching, double trenching and possibly multiple trenching, mode-field-diameters), the type of optical fiber (e.g., UBIF)), a category of the optical fiber (e.g., G.657.B3, etc.), the mode of the optical fiber, and the optical fiber buffer conditions, such as loose or tight buffered cable/drop. The optical fiber data may include other data pertaining to optical index profiles, the number of tight bends in the optical fiber, a distance between bends, the placement of the mapped bend radius relative to other bend(s) or mechanical twist(s), the distance of the mapped bend radius relative to other mechanical stresses, the optical transmitter and/or other components of a test system used.

The historical data may include data pertaining to the optical signal used to derive the mapping. For example, the optical signal data may include data pertaining to the wavelength of the optical signal, the power of the optical signal, and the modulation scheme. An optical signal characteristic (e.g., modulation, etc.) may be used based on an optical network type (e.g., Ethernet Passive Optical Network (EPON), Gigabit Passive Optical Network (GPON), etc.) in which the optical fiber under test is used. The historical data may include data pertaining to other parameters, such as environmental conditions (e.g., temperature, humidity above ground, in-ground, which can cause extra constraints, etc.).

The historical data also includes, as previously described, interference data, tight bend radius data, and lifetime data. The interference data includes interference values (e.g., maximum interference, minimum interference). The bend radius data includes bend radii values. The lifetime data includes an estimated length of time before an expected breakage occurs in the optical fiber. Additionally, or alternatively, the lifetime data includes a parts-per-million (PPM) failure rate.

Figure 6:
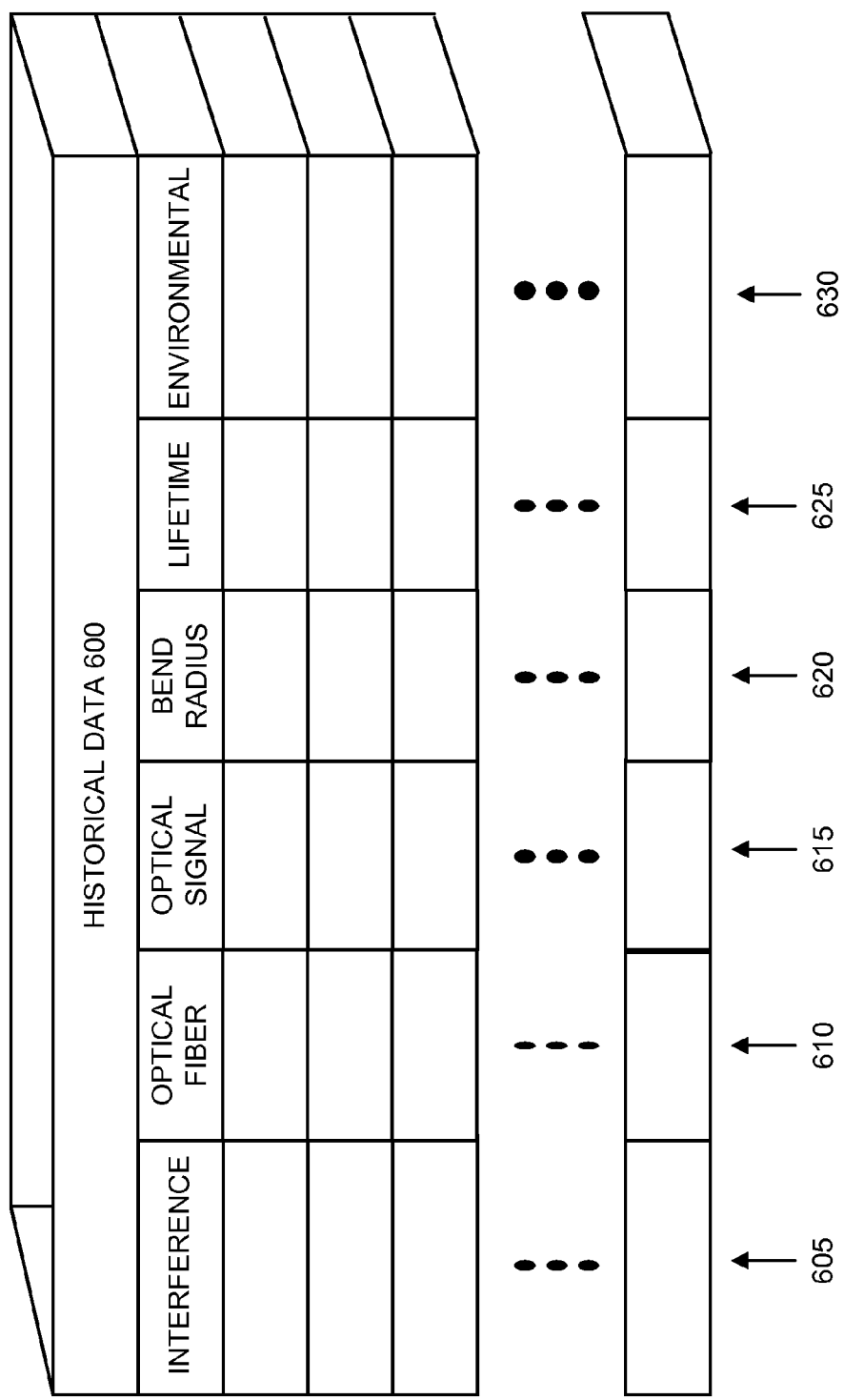
FIG. 6 is a diagram illustrating exemplary historical data.

FIG. 6 is a diagram illustrating exemplary historical data 600 in a table format. Historical data 600 includes interference data 605, optical fiber data 610, optical signal data 615, bend radius data 620, lifetime data 625, and environmental data 630, as previously described. In this format, a row may be considered an entry that maps interference data 605 to the other historical data. Other formats and/or data structures may be implemented. Additionally, according to other implementations, historical data 600 may include additional types of data, fewer types of data, and/or different types of data than illustrated in FIG. 6.

User device 105 may access historical data 600 and correlate degrees of interference values obtained from a test to other historical data 600 (e.g., bend radius data, etc.) based on comparing the degrees of interference values to interference data 605 and other historical data 600 (e.g., optical fiber data 610, etc.) to select the appropriate bend radius data 620, etc.

Optical transmitter/wavelength scanner 120 includes a component capable of generating and transmitting an optical signal. For example, optical transmitter/wavelength scanner 120 may be implemented as a wavelength-tunable laser source. The wavelength-tunable laser source may be capable of tuning to various bands and particular wavelength(s) in a band. For example, the bands may include the O-band (e.g., 1260-1360 nm), the E-band (e.g., 1360-1460 nm), the S-band (e.g., 1460-1530 nm), C-band (e.g., 1530-1565), the L-band (e.g., 1565-1625), and the U-band (e.g., 1625-1675 nm). A tester may select a particular band or range of wavelengths based upon, for example, ITU-T standards, such as the specifications applicable to Dense Wavelength Division Multiplexing (DWDM) applications. Optical transmitter/scanner 120 may include power adjustment capabilities. Optical transmitter/wavelength scanner 120 may also include wavelength scanning capabilities (e.g., narrowband scanning). Additionally, optical transmitter/scanner 120 may also provide different modulation schemes (e.g., non-return-to-zero (NRZ), return-to-zero (RZ), etc.), bore rates, etc.

Optical splitters 125 each include a component capable of splitting, combining, and/or providing an optical path for an optical signal. Referring to FIG. 1, optical splitters 125-1 and 125-4 are implemented as 1×2 splitters and optical splitters 125-2, 125-3, and 125-5 are implemented as 2×1 splitters (also known as optical recombiners).

Polarization controllers 130 each include a component capable of converting the polarization of an optical signal from one state to another. Polarization controllers 130 may also each include a component (e.g., a polarization analyzer) capable of measuring and/or analyzing polarization properties of an optical signal.

Optical isolator 135 includes a component capable of allowing the transmission of an optical signal in one direction. In view of the configuration of test system 100, optical isolator 135 prevents a reflected optical signal from propagating along the transmit path.

Optical receiver 140 includes a component capable of receiving an optical signal and performing a measurement. For example, optical receiver 140 may be implemented as an optical power meter or an optical spectrum analyzer.

Optical fiber 145 provides an optical connection between the various components of test system 100. According to an exemplary implementation, optical fiber 145 is a single-mode fiber (e.g. ITU-T G.652.D standard, etc.). Optical fiber 165 is the device under test. For example, optical fiber 165 may be implemented as a UBIF or a BIF. Depending on the test case, optical fiber 165 may have various lengths (e.g., 300-500 meters).

FIGS. 2A-2F are diagrams illustrating an exemplary process in which test system 100 is used to perform measurements to estimate bend radius, lifetime, failure rate, or some combination thereof, in relation to the optical fiber under test. User device 105 and other components of test system 100 may operate according to feedback loops and/or test configuration information.

Figure 2A:
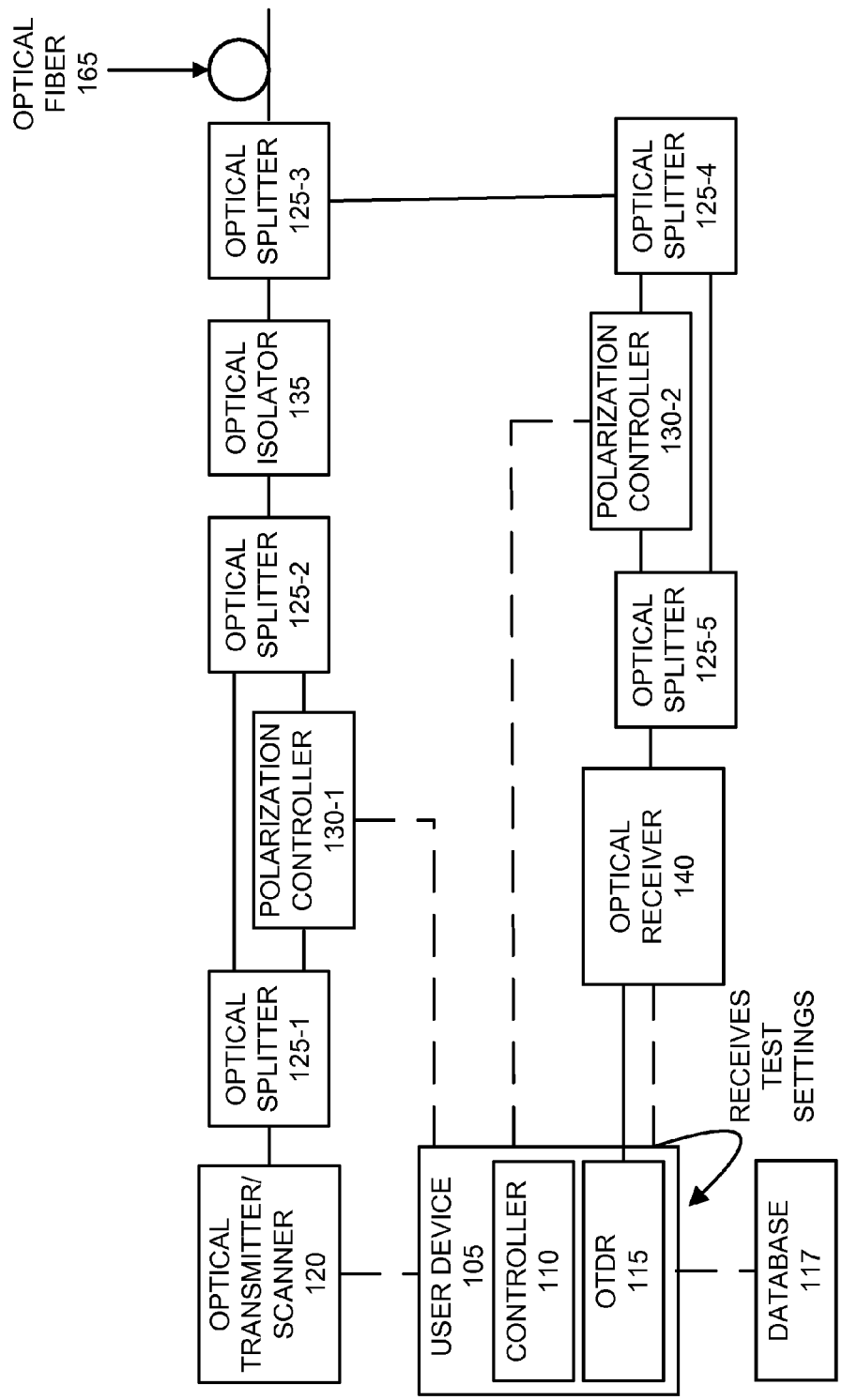
FIGS. 2A-2F are diagrams illustrating an exemplary process in which the test system is used to perform measurements of interference to estimate a bend radius, a lifetime, a failure rate, or some combination thereof in relation to the optical fiber under test.

Referring to FIG. 2A, a user inputs via user device 105 various settings pertaining to the test. As previously described, user device 105 includes various user interfaces to allow a user to control other components of test system 100 and conduct tests. For example, the user interface also allows the user to enter and/or select information to configure one or multiple other components of test system 100. For example, the user interface allows the user to set parameters associated with optical transmitter/scanner 120, such as wavelength and power. The user may also set other parameters, such as, for example, modulation of the optical signal, number of pulses or duration of emission, etc. Also, for example, the user interface may allow the user to set parameters associated with polarization controllers 130. For example, the user may set a polarization state for polarization controllers 130. The user may also set parameters to control a feedback loop, such as the rotation of a polarization state to cause alignment or de-alignment with respect to optical signals propagating through polarization controllers 130.

The user interface may allow the user to control optical receiver 140. For example, the user may set parameters relating to calculating a maximum interference, a minimum interference, or both based upon the interference patterns, relative to an optical signal received. The user interface may also allow the user to set parameters relating to calculating a location of a tight bend, consecutive tight bends, etc., in the optical fiber under test. Additionally, the user interface also allows the user to enter and/or select information pertaining to the optical fiber under test (e.g., type, model, manufacturer, category, etc.).

Figure 2B:
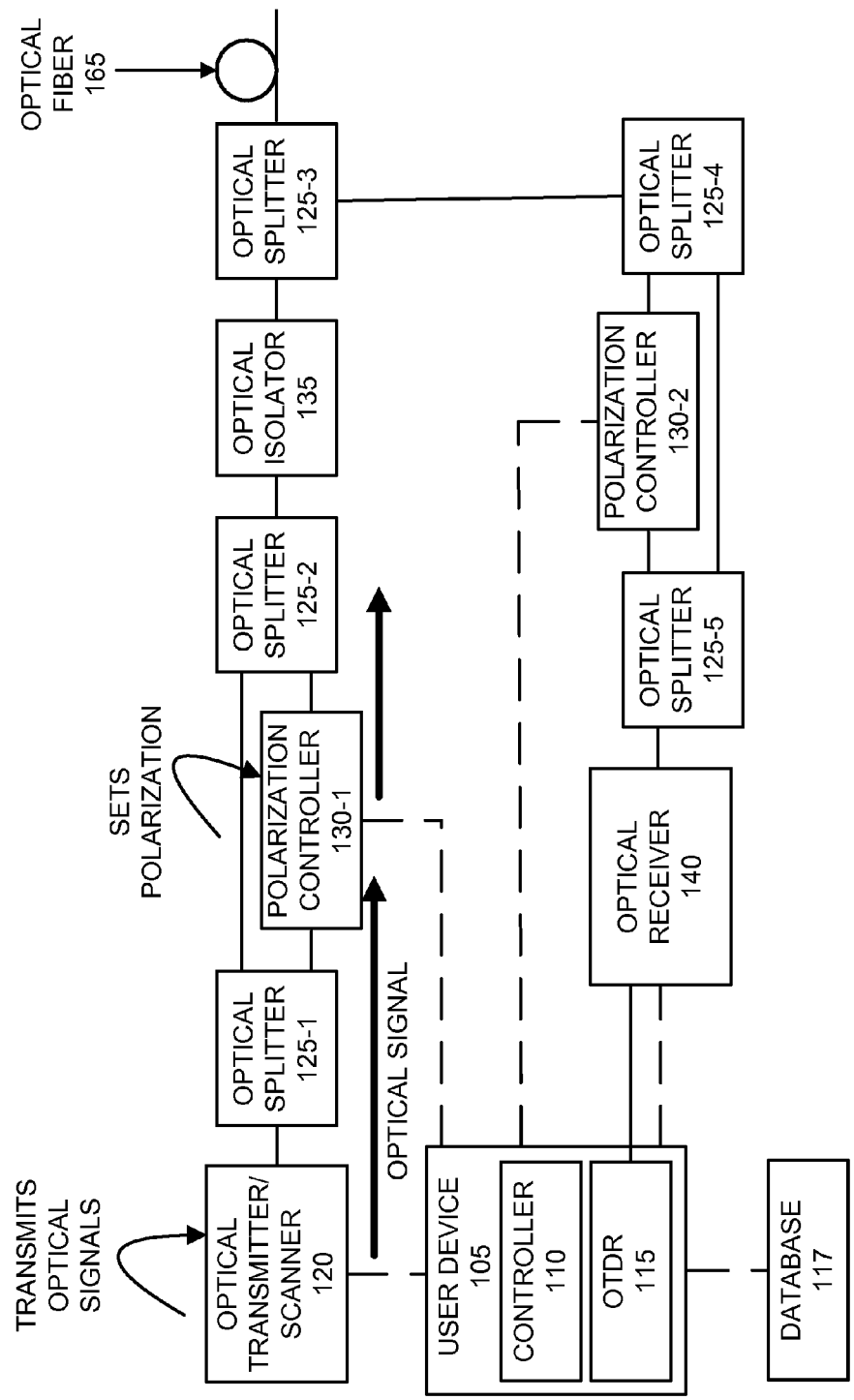

Referring to FIG. 2B, assume the user begins the test and test system 100 operates based on the user settings. For example, optical transmitter/scanner 120 transmits an optical signal having optical properties (e.g., wavelength, power, etc.) specified by the user. The optical signal propagates to optical splitter 125-1. As previously described, optical splitter 125-1 is implemented as a 1×2 splitter. Optical splitter 125-1 splits the optical signal into two legs. The first leg of the optical signal propagates directly to optical splitter 125-2 (e.g., an optical recombiner). The second leg of the optical signal propagates to optical splitter 125-2 via polarization controller 130-1. According to an exemplary implementation, assume that polarization controller 130-1 sets the polarization state of the second leg to a polarization state that is orthogonal to the first leg. For example, the multiple modes may be implemented as a horizontal mode and a vertical mode.

Figure 2C:
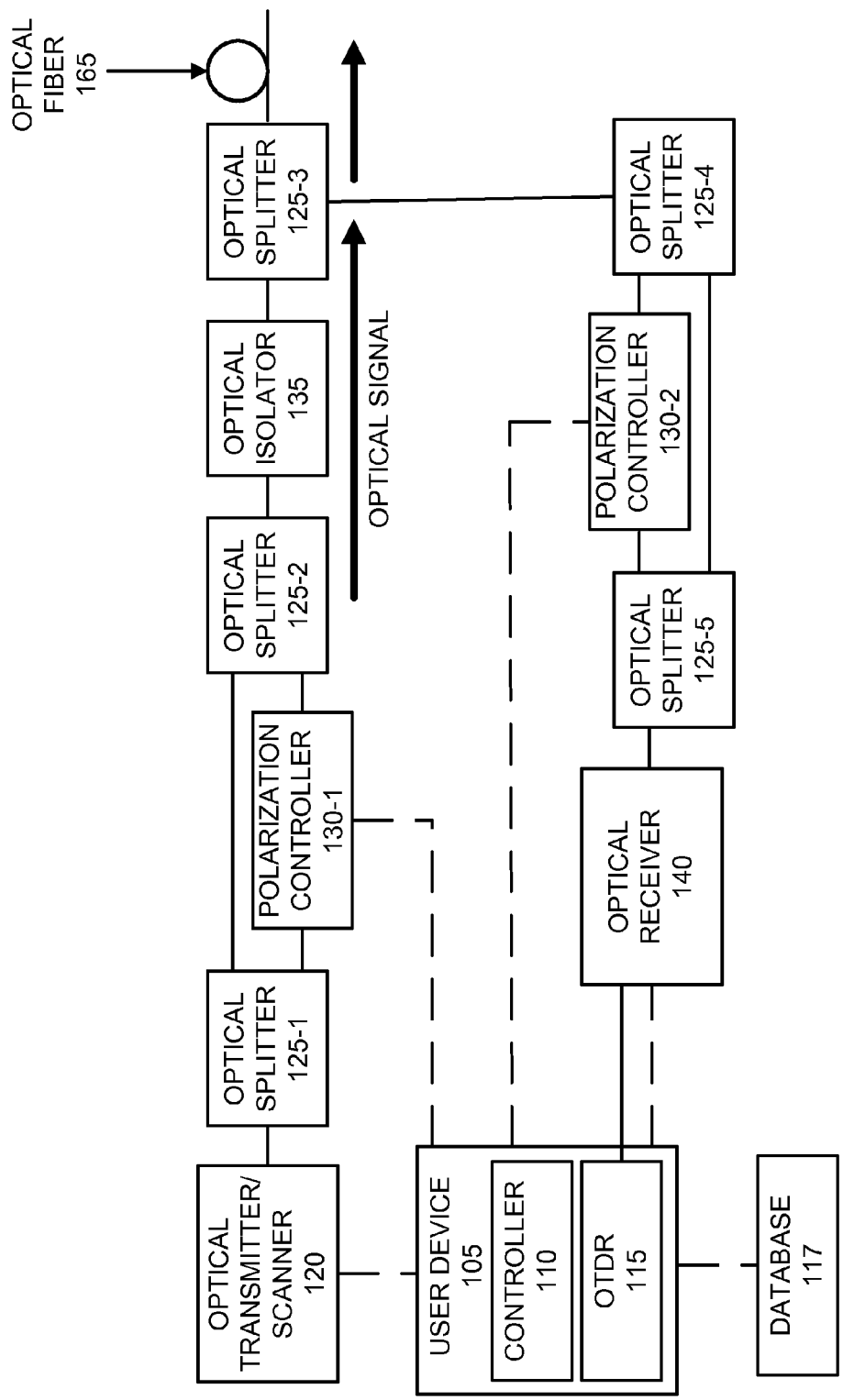

Referring to FIG. 2C, the legs of the optical signal are received by optical splitter 125-2. As previously described, optical splitter 125-2 is implemented as a 2×1 splitter. Optical splitter 125-2 combines the legs of the optical signal and outputs an optical signal that propagates to optical isolator 135. The optical signal propagates through optical isolator 135 to optical splitter 125-3. As previously described, optical splitter 125-3 is implemented as a 2×1 splitter. Optical splitter 125-3 allows the optical signal to propagate to optical fiber 165. The optical signal propagates through optical fiber 165 and a tight bend. The tight bend causes an alteration to the polarization of the optical signal based on the birefringence at the stress point.

Figure 2D:
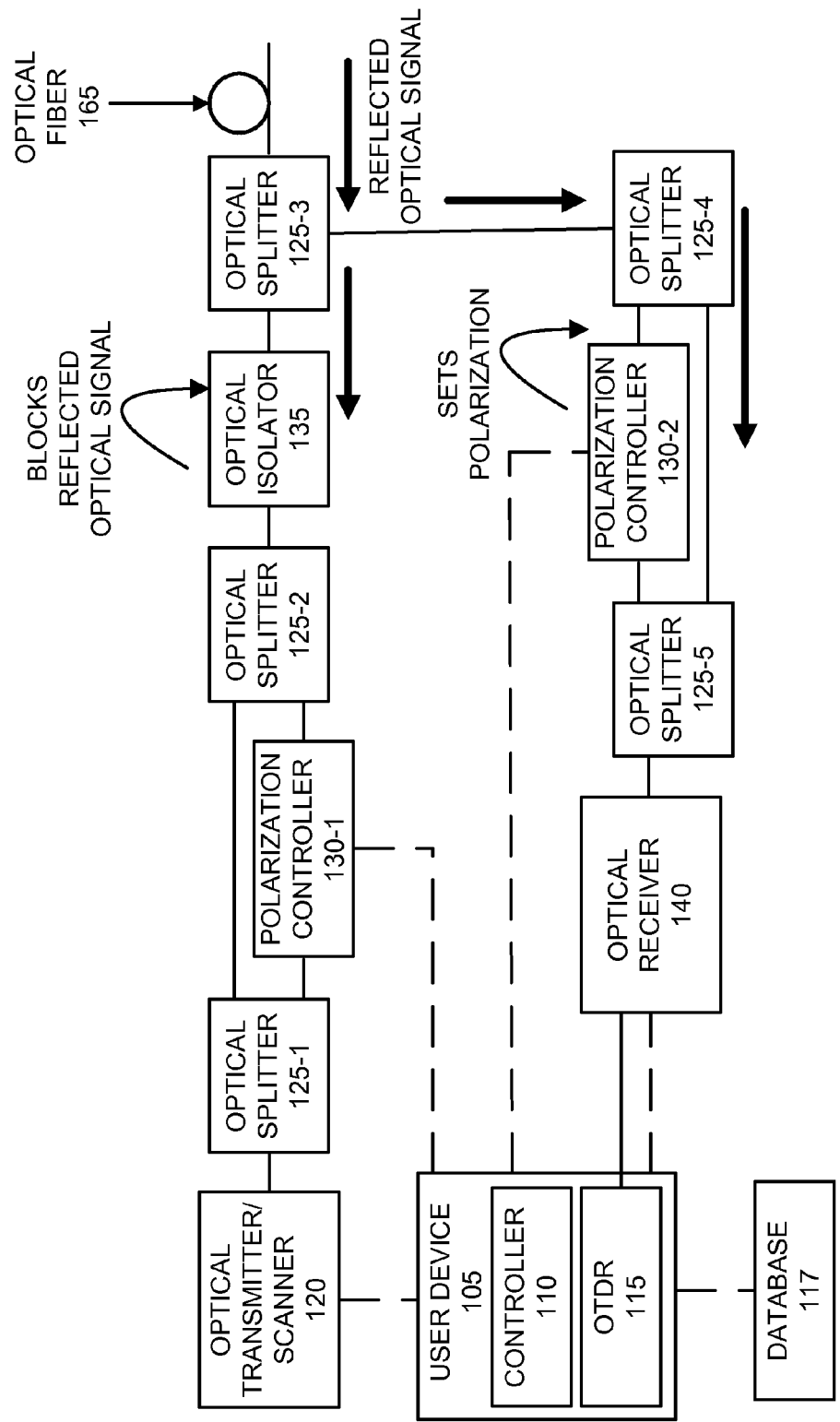

Referring to FIG. 2D, a reflected optical signal propagates to optical splitter 125-3. Optical splitter 125-3 splits the reflected optical signal in which a reflected optical signal propagates to optical isolator 135 and a reflected optical signal propagates to optical splitter 125-4. As illustrated, optical isolator 135 blocks the reflected optical signal to prevent the reflected optical signal from further propagating along the transmit path. As previously described, optical splitter 125-4 is implemented as a 1×2 splitter. Optical splitter 125-4 splits the reflected optical signal into two legs. The first leg of the optical signal propagates directly to optical splitter 125-5. The second leg of the optical signal propagates to optical splitter 125-5 via polarization controller 130-2. According to an exemplary implementation, assume that polarization controller 130-2 sets the polarization state of the second leg. For example, assume that the reflected optical signal from the tight bend has two polarization states. In this regard, points in the reflected signal may be set by polarization controller 130-2 such that the polarization states are orthogonal and may yield minimal interference or points in the reflected signal optical signal may be set such that the polarization states are aligned and may yield maximum interference. User device 105 (e.g., controller 110) may control polarization controller 130-2 to rotate, in a step-wise fashion for a total of 360 degrees, and appropriately set the polarization state of the reflected optical signal. As described below, during this time, optical receiver 140 measures the power of the reflected optical signal with respect to the degree of interferences.

Figure 2E:
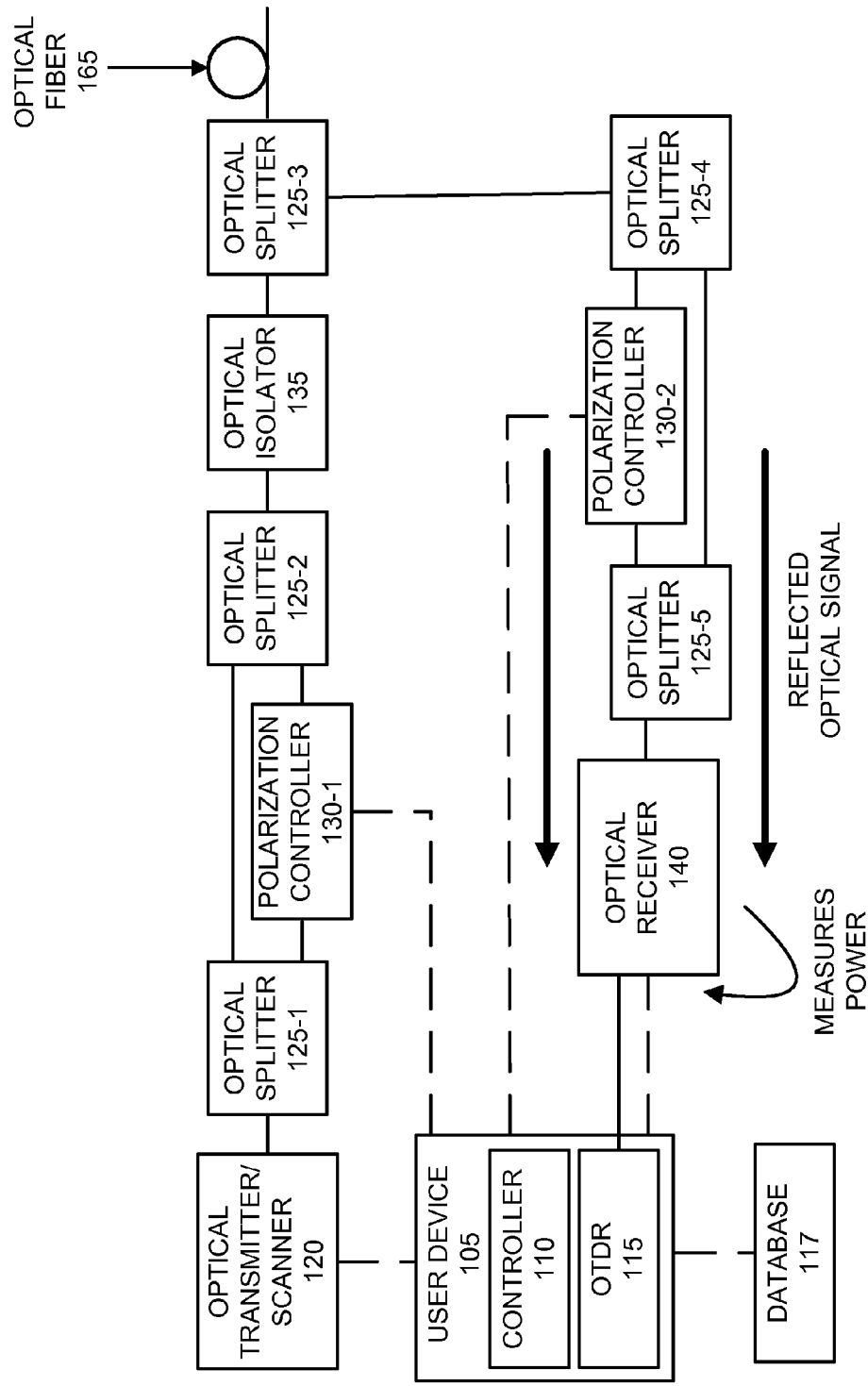

Referring to FIG. 2E, the legs of the reflected optical signal are received by optical splitter 125-5. As previously described, optical splitter 125-5 is implemented as a 2×1 splitter. Optical splitter 125-5 combines the legs of the reflected optical signal and outputs a reflected optical signal that propagates to optical receiver 140. Optical receiver 140 measures power of the reflected optical signal over time. These power values are provided to user device 105.

Figure 2F:
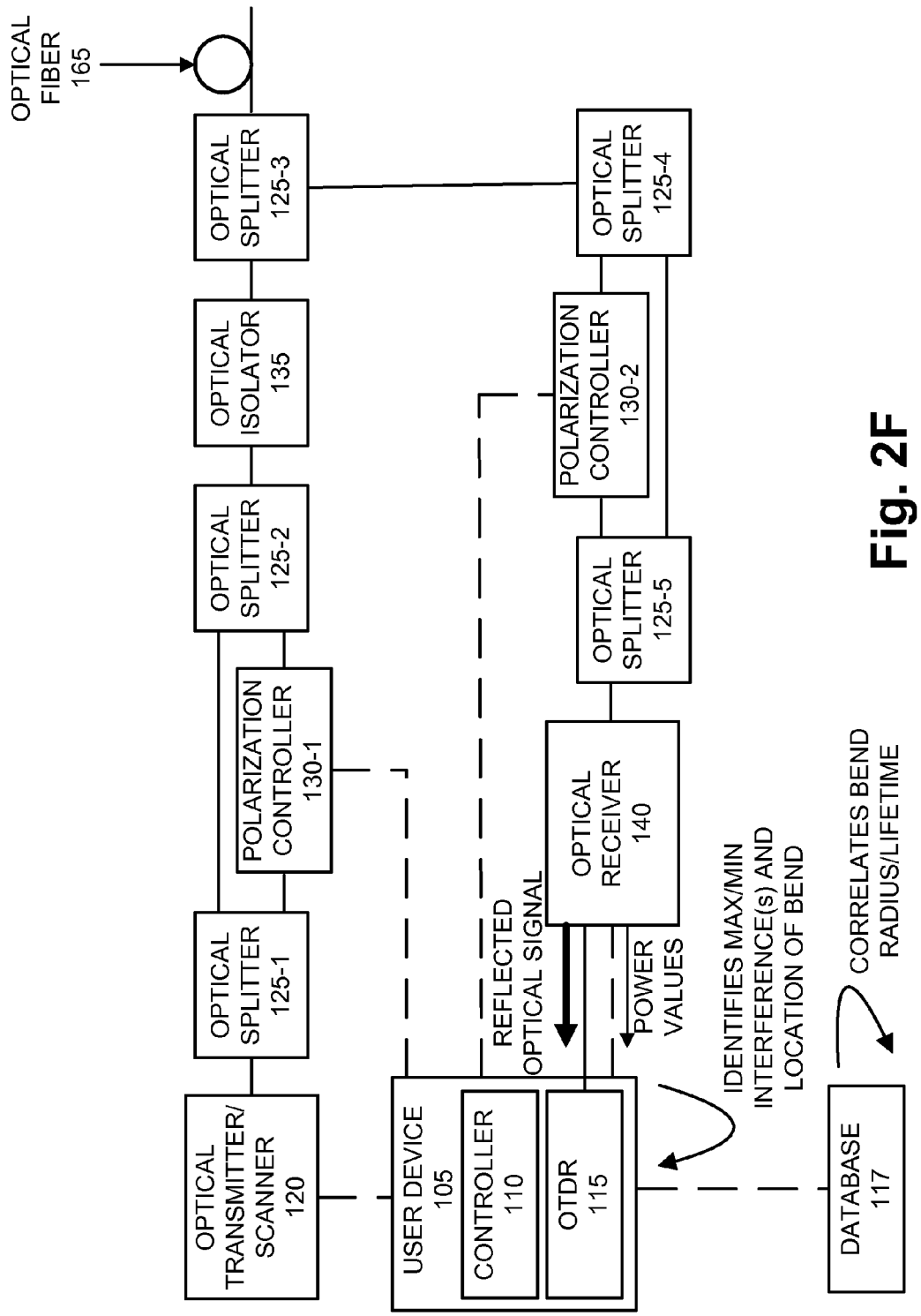

Referring to FIG. 2F, user device 105 receives power values and stores the power values as part of the test data. User device 105 identifies an instance of maximum interference or minimum interference. OTDR 115 calculates a location of the tight bend based on the signature of the reflected optical signal. The signature may include a sudden increase or decrease in optical power and identified as a non-reflective event anomaly corresponding to the tight bend in optical fiber 165. OTDR 115 also uses the times associated with the launch of the optical signal and the return to identify the location of the tight bend and bends.

User device 105 accesses database 117. User device 105 selects a mapping that corresponds to the parameters (e.g., user settings) and results of the test. For example, user device 105 identifies an entry in database 117 that matches to the measured interference value, type of fiber, and the characteristics of the optical signal (e.g., wavelength, etc.). User device 105 outputs to the user one or more results, such as the bend radius of the tight bend, the lifetime of the optical fiber under test, and/or a failure rate associated with the optical fiber under test.

In some instances, the process described and illustrated in FIGS. 2A-2F may continue across one or more bands, sub-bands, etc., until the test is completed.

Figure 3:
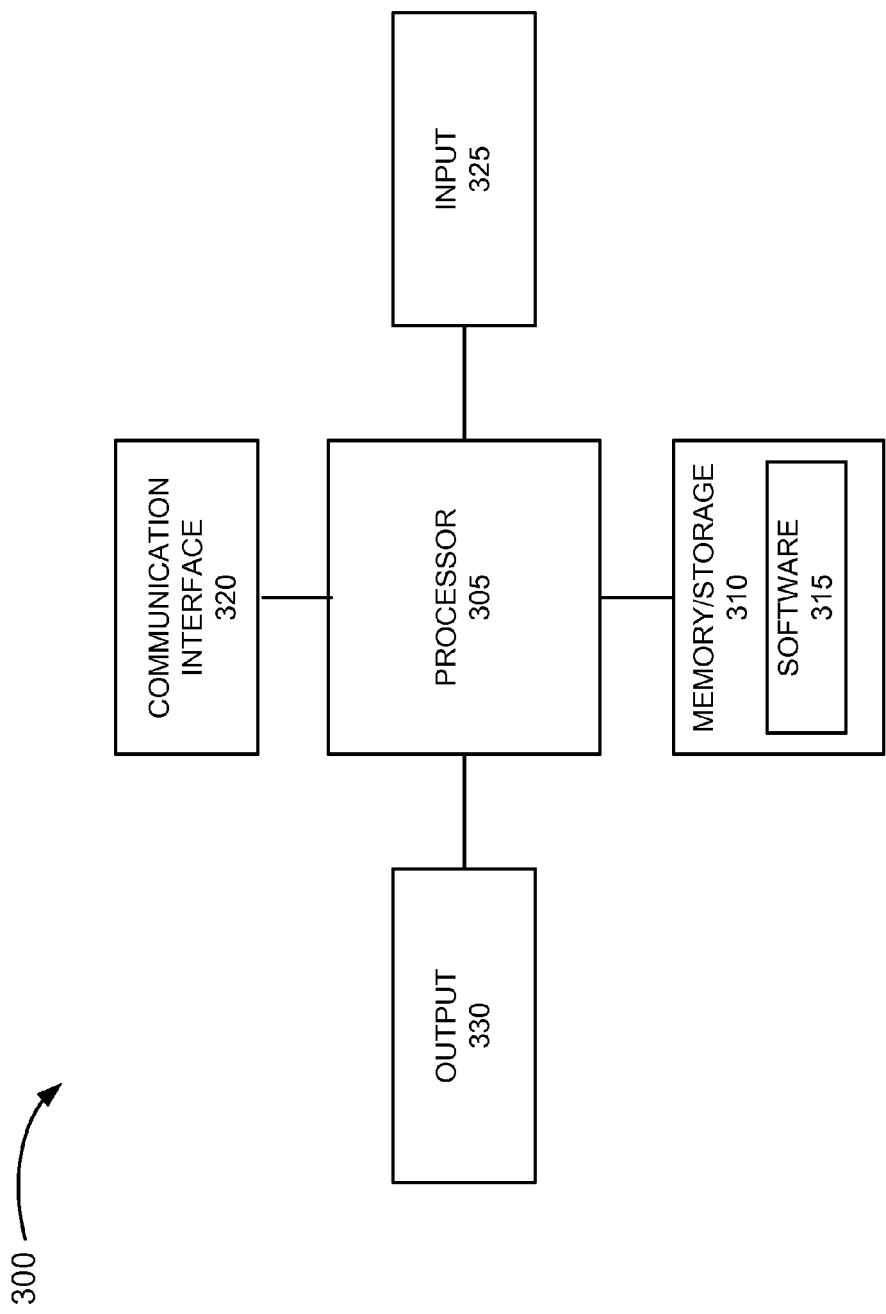
FIG. 3 is a diagram illustrating exemplary components of a device that may correspond to one or more of the devices of the test system.

FIG. 3 is a diagram illustrating exemplary components of a device 300 that may correspond to one or more of the devices of the test system 100. As illustrated, according to an exemplary embodiment, device 300 includes a processor 305, memory/storage 310 storing software 315, a communication interface 320, an input 325, and an output 330. According to other embodiments, device 300 may include fewer components, additional components, different components, and/or a different arrangement of components than those illustrated in FIG. 3 and described herein.

Processor 305 includes one or multiple processors, microprocessors, data processors, co-processors, application specific integrated circuits (ASICs), controllers, programmable logic devices, chipsets, field-programmable gate arrays (FPGAs), application specific instruction-set processors (ASIPs), system-on-chips (SoCs), central processing units (e.g., one or multiple cores), microcontrollers, and/or some other type of component that interprets and/or executes instructions and/or data. Processor 305 may be implemented as hardware (e.g., a microprocessor, etc.) or a combination of hardware and software (e.g., a SoC, an ASIC, etc.). Processor 305 may include one or multiple memories (e.g., memory/storage 310), etc.

Processor 305 may control the overall operation or a portion of operation(s) performed by device 300. Processor 305 may perform one or multiple operations based on an operating system and/or various applications or programs (e.g., software 315). Processor 305 may access instructions from memory/storage 310, from other components of device 300, and/or from a source external to device 300 (e.g., a network, another device, etc.).

Memory/storage 310 includes one or multiple memories and/or one or multiple other types of storage mediums. For example, memory/storage 310 may include one or multiple types of memories, such as, random access memory (RAM), dynamic random access memory (DRAM), cache, read only memory (ROM), a programmable read only memory (PROM), a static random access memory (SRAM), a single in-line memory module (SIMM), a phase-change memory (PCM), a dual in-line memory module (DIMM), a flash memory, and/or some other type of memory. Memory/storage 310 may include a hard disk (e.g., a magnetic disk, an optical disk, a magneto-optic disk, a solid state disk, etc.), a Micro-Electromechanical System (MEMS)-based storage medium, and/or a nanotechnology-based storage medium. Memory/storage 310 may include drives for reading from and writing to the storage medium.

Memory/storage 310 may be external to and/or removable from device 300, such as, for example, a Universal Serial Bus (USB) memory stick, a dongle, a hard disk, mass storage, off-line storage, or some other type of storing medium (e.g., a compact disk (CD), a digital versatile disk (DVD), a Blu-Ray® disk (BD), etc.). Memory/storage 310 may store data, software, and/or instructions related to the operation of device 300.

Software 315 includes an application or a program that provides a function and/or a process. Software 315 may include firmware. Communication interface 320 permits device 300 to communicate with other devices, networks, and/or systems. For example, with reference to user device 105, communication interface 320 permits user device 105 to communicate with a component of test system 100. By way of further example, communication interface 320 may include a communication interface to communicate with optical transmitter/scanner 120, etc. Communication interface 320 may include a wireless interface and/or a wired interface. Communication interface 320 includes a transmitter, a receiver, and/or a transceiver.

Input 325 provides an input into device 300. For example, input 325 may include a keyboard, a mouse, a display, a touchscreen, a touchless screen, a button, a switch, an input port, speech recognition logic, and/or some other type of visual, auditory, tactile, etc., input component. Output 330 provides an output from device 300. For example, output 330 may include a speaker, a display, a touchscreen, a touchless screen, a light, an output port, and/or some other type of visual, auditory, tactile, etc., output component.

Device 300 may perform processes and/or functions, as described herein, in response to processor 305 executing software 315 stored by memory/storage 310. By way of example, the instructions may be read into memory/storage 310 from another memory/storage 610 or read from another device via communication interface 320. The instructions stored by memory/storage 310 may cause processor 305 to perform one or more processes described herein. Alternatively, for example, according to other implementations, device 300 may perform one or more processes described herein based on the execution of hardware (processor 305, etc.), the execution of firmware with hardware, or the execution of software and firmware with hardware.

Figure 4A:
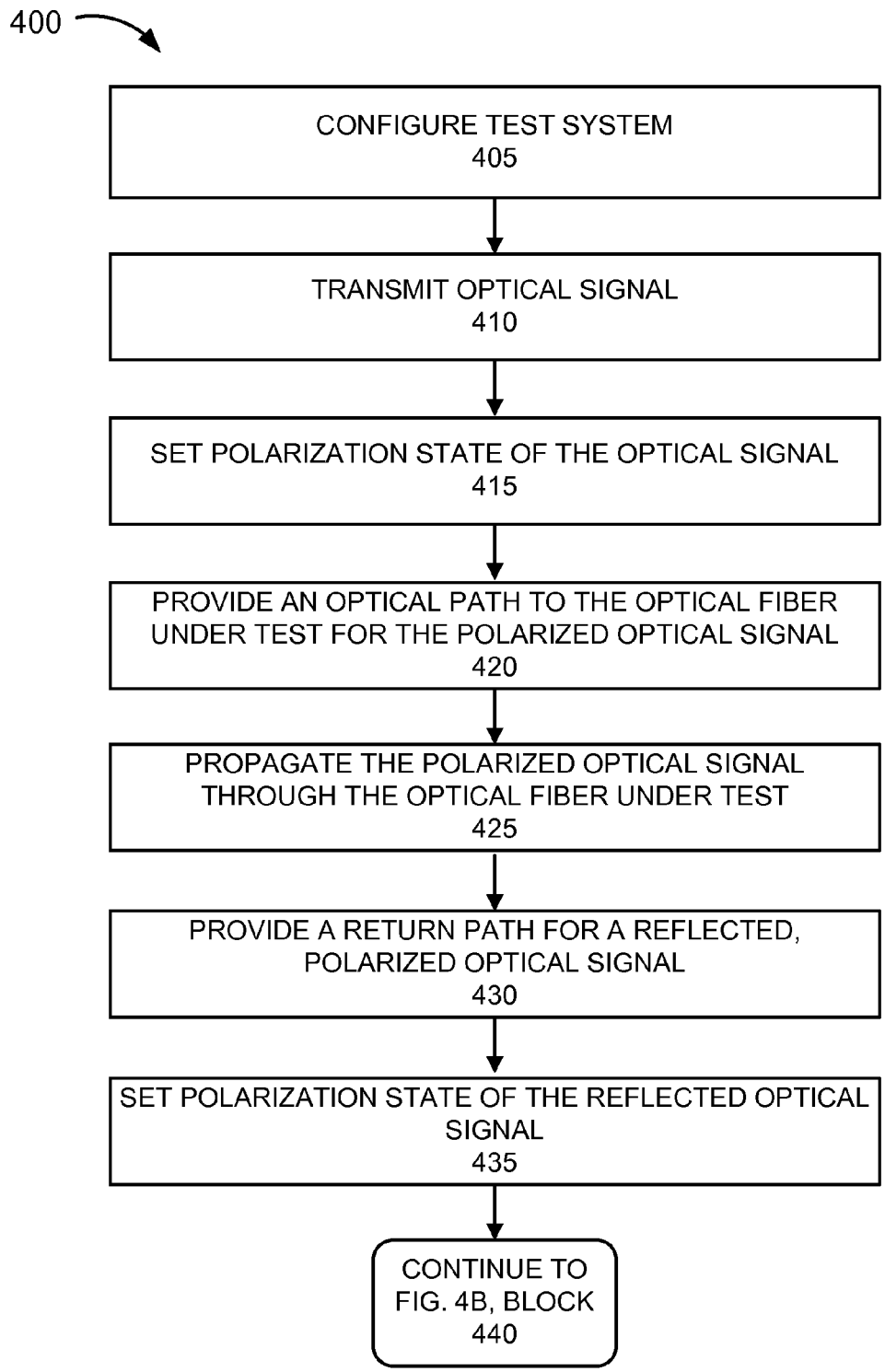
FIGS. 4A and 4B are flow diagrams illustrating an exemplary process for measuring interference and correlating the interference to estimate a bend radius, a lifetime, a failure rate, or some combination thereof in relation to an optical fiber under test.
Figure 4B:
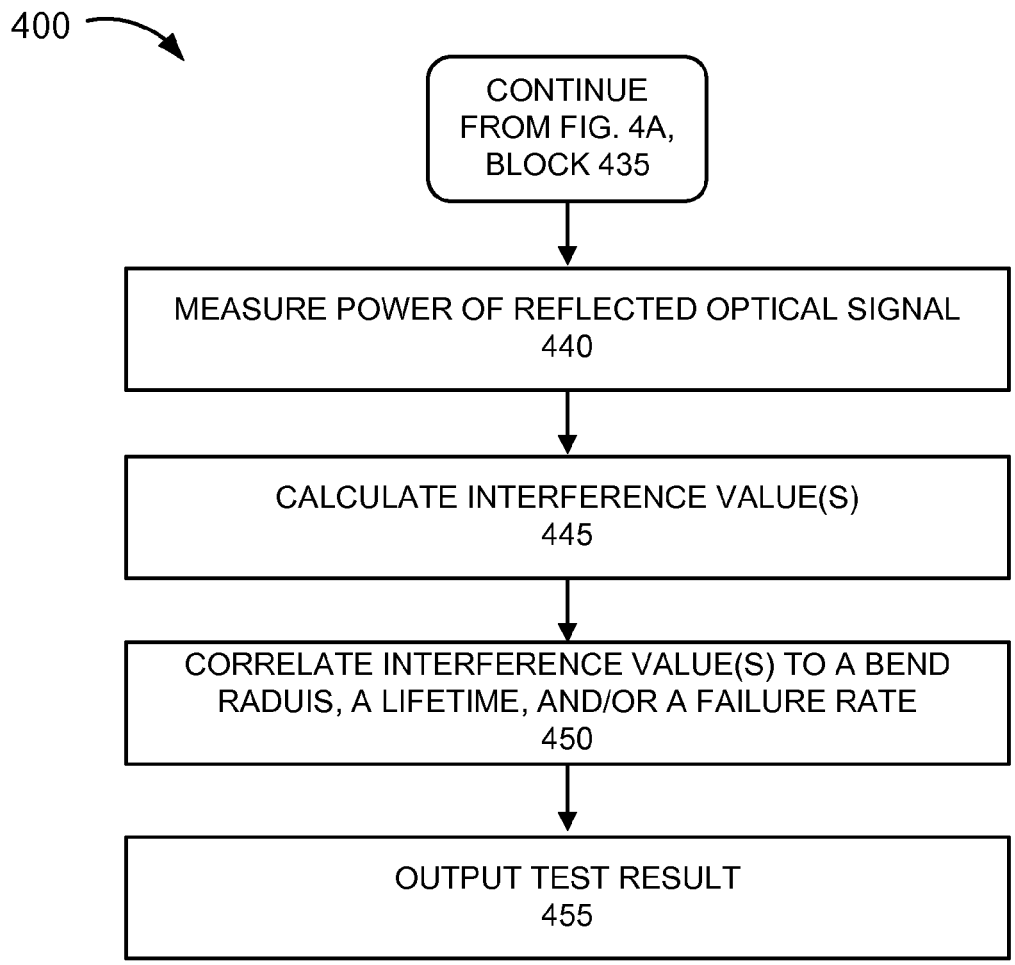

FIGS. 4A and 4B are flow diagrams illustrating an exemplary process 400 to estimate the bend radius, the lifetime, the failure rate, or some combination thereof, of an optical fiber under test. For example, process 400 provides for the measuring of interference and a correlation to bend radius, lifetime, failure rate, or some combination thereof. Process 400 is performed by test system 100. Process 400 may be performed in relation to bands "O" through "U."

Referring to FIG. 4A, process 400 begins with configuring the test system (block 405). For example, as previously described, a user inputs configuration parameters pertaining to components of test system 100 (e.g., optical transmitter/scanner 120, polarization controller 130, etc.), and information pertaining to the optical fiber under test (e.g., optical fiber data).

In block 410, an optical signal is transmitted. For example, as previously described, optical transmitter/scanner 120 is configured to transmit an optical signal having user-configurable characteristics (e.g., wavelength, power, etc.).

In block 415, the polarization state of the optical signal is set. For example, as previously described, the optical signal propagates to polarization controller 130-1 via optical splitter 125-1. Optical splitter 125-1 splits the optical signal into two legs. Polarization controller 130-1 sets the polarization state of one of the legs of the optical signal. According to an exemplary implementation, polarization controller 125-1 sets the polarization state of the leg to be orthogonal to the other leg.

In block 420, an optical path to the optical fiber under test is provided for the polarized optical signal. For example, as previously described, test system 100 includes an optical splitter 125-2 that receives each leg (i.e., mode) of the optical signal and provides an optical path to the optical fiber under test.

In block 425, the polarized optical signal propagates through the optical fiber under test. For example, as previously described, the polarized optical signal propagates through optical fiber 165. Optical fiber 165 has a tight bend. According to an exemplary implementation, optical fiber 165 is a bend-insensitive fiber or an ultra-bend insensitive fiber. The polarization of the polarized optical signal is altered based on the birefringence associated with the tight bend.

In block 430, an optical path for a reflected, polarized optical signal is provided. For example, as previously described, test system 100 permits the reflected, polarized optical signal, having propagated through the optical fiber under test, to propagate along a return path. For example, optical splitter 125-3 provides an optical path that allows the reflected, polarized optical signal to propagate along the return path. Optical isolator 135 prevents the reflected, polarized optical signal from propagating along a transmit path.

In block 435, the polarization state of the reflected, polarized optical signal is set. For example, optical splitter 125-4 receives the reflected, polarized optical signal in the return path and splits the reflected, polarized optical signal into two legs. The first leg of the reflected, polarized optical signal propagates directly to optical splitter 125-5. The second leg of the optical signal propagates to optical splitter 125-5 via polarization controller 130-2. Polarization controller 130-2 sets the polarization state to an orthogonal state or aligns the polarization state to produce a minimum interference or a maximum interference.

Referring to FIG. 4B, in block 440, the power of the reflected, polarized optical signal is measured. For example, as previously described, optical splitter 125-5 combines the legs of the reflected, polarized optical and outputs to optical receiver 140. Optical receiver 140 measures the power of the reflected, polarized optical signal. Optical receiver 140 outputs the power values to user device 105. Optical receiver 140 also outputs the reflected, polarized optical signal to OTDR 115.

In block 445, the interference values are calculated. For example, as previously described, user device 105 identifies an instance of maximum interference, minimum interference, or other degree of interference. For example, the tighter the bend, the greater the material-mechanical stress that is exerted in the optical fiber and the larger degree of birefringence that is produced. As user device 105 controls the amount of polarization controller rotation and the received interference patterns (which may constitute the maximum and minimum patterns at a cross section of a tight bend), and the received power changes at the cross-section of the tight bend with interference change during the polarization adjustment, user device 105 is capable of calculating the degree of interference. OTDR 115 calculates a location of the tight bend based on the signature of the reflected, polarized optical signal.

In block 450, the interference value(s) are correlated to a bend radius, a lifetime, and/or a failure rate. For example, as previously described, user device 105 accesses the historical data stored by database 117. User device 105 selects an entry in database 117 that matches the measured interference value(s) and other parameters associated with the test performed. The entry in database 117 maps the interference value(s) to a bend radius, a lifetime, and/or a failure rate pertaining to the optical fiber under test.

In block 455, a test result is output. For example, user device 105 outputs the test result that indicates a bend radius, a lifetime, and/or a failure rate pertaining to the optical fiber under test.

Although FIGS. 4A and 4B illustrate an exemplary process 400, according to other implementations, process 400 may include additional operations, fewer operations, and/or different operations than those illustrated and described herein.

Figure 5:
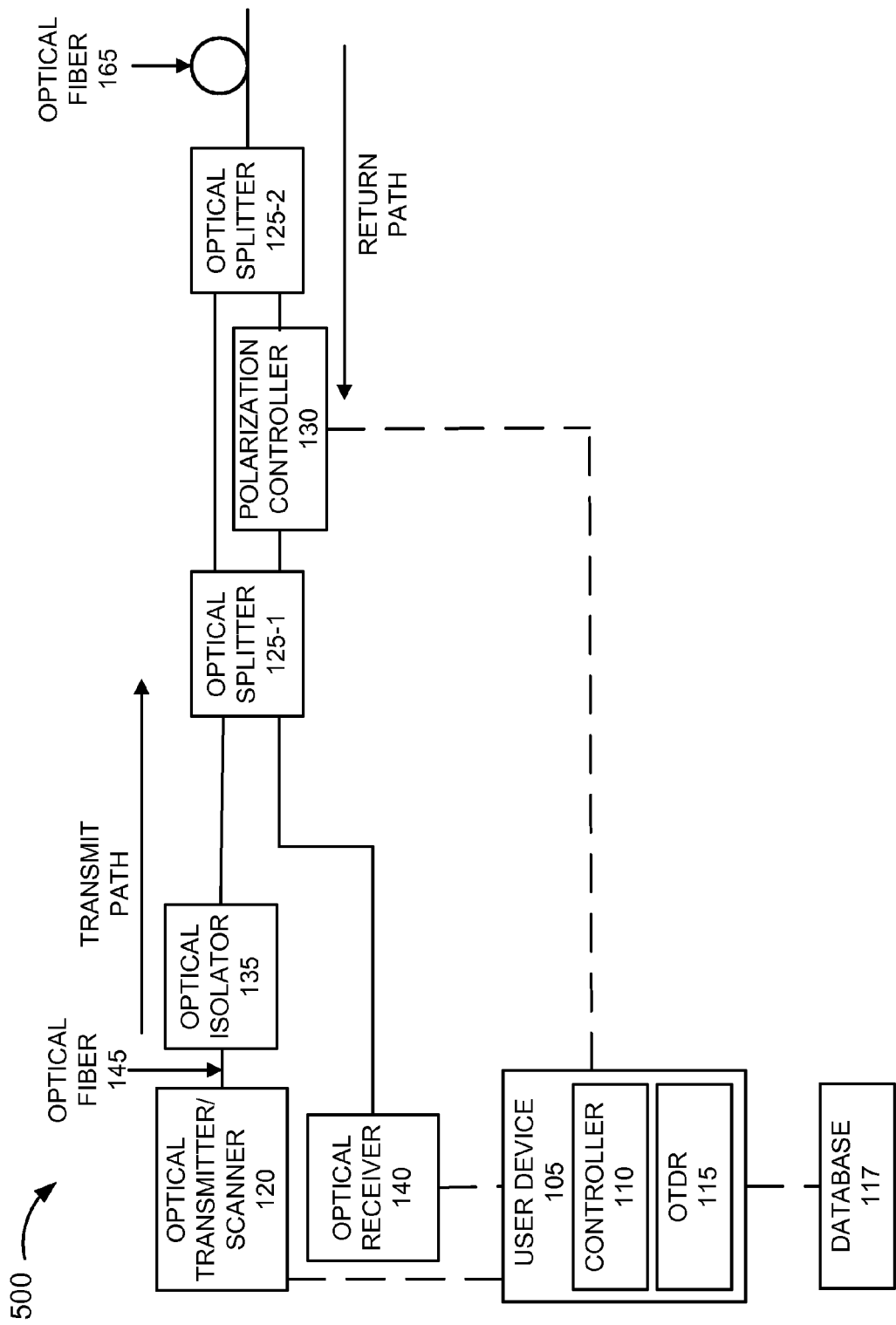
FIG. 5 is a diagram illustrating another exemplary embodiment of a test system capable of testing an optical fiber under test to estimate a bend radius, a lifetime, a failure rate, or some combination thereof.

FIG. 5 is a diagram illustrating another exemplary embodiment of a test system 500 capable of testing an optical fiber under test to estimate a bend radius, a lifetime, a failure rate, or some combination thereof. Test system 500 includes components previously described. However, as illustrated in FIG. 5, test system 500 has a different configuration than the configuration of test system 100. Additionally, optical splitter 125-1 may be implemented as a 2×2 optical splitter. Additionally, according to an exemplary implementation, optical isolator 135 may be implemented as an optical filter.

According to an exemplary process, optical transmitter/wavelength scanner 120 transmits an optical signal, which has a single polarization, along the transmit path. The optical signal propagates along the transmit path via optical isolator 135 and optical splitters 125-1 and 125-2. The optical signal continues to propagate in optical fiber under test 165 that includes a tight bend. Due to the mechanical stresses associated with the tight bend, a reflected optical signal having two polarization states is generated. The reflected optical signal propagates along the transmit path. However, optical isolator 135 prevents the reflected optical signal from reaching optical transmitter/wavelength scanner 120. Additionally, the reflected signal propagates along the return path via polarization controller 130. Similar to that previously described with respect to polarization controller 130-2 of FIGS. 2A-2F, polarization controller 130 of FIG. 5 may align or de-align the reflected optical signal to produce a degree of interference (e.g., minimum interference or maximum interference). The remaining steps of this process are the same as previously described.

The foregoing description of embodiments provides illustration, but is not intended to be exhaustive or to limit the embodiments to the precise form disclosed. Accordingly, modifications to the embodiments described herein may be possible.

The terms "a," "an," and "the" are intended to be interpreted to include one or more items. Further, the phrase "based on" is intended to be interpreted as "based, at least in part, on," unless explicitly stated otherwise. The term "and/or" is intended to be interpreted to include any and all combinations of one or more of the associated items.

In addition, while a series of blocks has been described with regard to the process illustrated in FIGS. 4A and 4B, the order of the blocks may be modified according to other embodiments. Further, non-dependent blocks may be performed in parallel. Additionally, other processes described in this description may be modified and/or non-dependent operations may be performed in parallel.

The embodiments described herein may be implemented in many different forms of software, firmware, and/or hardware. For example, a process or a function may be implemented as "logic" or as a "component." This logic or this component may include hardware (e.g., processor 305, etc.) or a combination of hardware and software (e.g., software 315). The embodiments have been described without reference to the specific software code since software can be designed to implement the embodiments based on the description herein.

In the preceding specification, various embodiments have been described with reference to the accompanying drawings. It will, however, be evident that various modifications and changes may be made thereto, and additional embodiments may be implemented, without departing from the broader scope of the invention as set forth in the claims that follow. The specification and drawings are accordingly to be regarded as illustrative rather than restrictive.

In the specification and illustrated by the drawings, reference is made to "an exemplary embodiment," "an embodiment," "embodiments," etc., which may include a particular feature, structure or characteristic in connection with an embodiment(s). However, the use of the phrase or term "an embodiment," "embodiments," etc., in various places in the specification does not necessarily refer to all embodiments described, nor does it necessarily refer to the same embodiment, nor are separate or alternative embodiments necessarily mutually exclusive of other embodiment(s). The same applies to the term "implementation," "implementations," etc.

No element, act, or instruction described in the present application should be construed as critical or essential to the embodiments described herein unless explicitly described as such.

What is claimed is:

1. A method comprising:
    transmitting an optical signal, via a test system, toward an optical fiber under test that has a tight bend;
    setting a state of polarization of the optical signal before the optical signal reaches the optical fiber under test;
    generating a first splitting of a reflected portion of the optical signal, which is caused by the tight bend, into two legs;
    setting a state of polarization of the reflected portion of the optical signal that propagated through the optical fiber under test, wherein setting the state of the polarization of the reflected portion comprises setting the state of polarization of one of the two legs of the reflected portion of the optical signal to an orthogonal state or an aligned state relative to the other leg of the reflected portion of the optical signal;
    measuring instances of power of the reflected portion of the optical signal;
    calculating interference values of the reflected portion of the optical signal caused by the tight bend based on the measured instances of power;
    storing interference values mapped to at least one of bend radii values, lifetime values, or failure rate values pertaining to optical fibers;

selecting a match between at least one of the calculated interference values and one of the stored interference values; and outputting a result that includes at least one of a bend radius value, a lifetime value, or a failure rate that applies to the optical fiber under test.

2. The method of claim 1, wherein the optical fiber under test is a bend insensitive fiber or an ultra-bend insensitive fiber, and wherein the at least one of the calculated interference values includes a maximum interference value or a minimum interference value.

3. The method of claim 1, further comprising:
generating a second splitting of the optical signal into two legs before setting the state of polarization of the optical signal and before the optical signal reaches the optical fiber under test, and wherein the setting the state of polarization of the optical signal comprises:
setting one of the two legs of the split optical signal, produced by the second splitting, to an orthogonal state relative to the other leg of the split optical signal, produced by the second splitting.

4. The method of claim 1, further comprising:
storing optical signal data that is mapped to stored interference values, wherein the optical signal data indicates wavelengths, power values, and modulation schemes of optical signals.

5. The method of claim 1, further comprising:
combining the two legs after the setting of the one of the two legs.

6. The method of claim 1, further comprising:
blocking another reflected portion of the optical signal from propagating along a transmit path.

7. The method of claim 1, further comprising:
storing optical fiber data pertaining to previously tested optical fibers, wherein the optical fiber data is mapped to the interference values.

8. The method of claim 1, further comprising:
calculating a location of the tight bend based on characteristics of the reflected portion of the optical signal.

9. A test system comprising:
a user device comprising:
a communication interface;
one or more memories that store instructions; and
one or more processors that execute the instructions to:
receive a selection of parameters directed to conducting a test of an optical fiber under test, wherein the optical fiber under test has a tight bend and the optical fiber under test includes one of a bend insensitive fiber or an ultra-bend insensitive fiber;
cause, via the communication interface, other test components of the test system to conduct the test based on the parameters, the other test components comprising:
an optical signal source capable of transmitting an optical signal, having a wavelength between an O-band through a U-band, through the optical fiber under test;
polarization controllers capable of setting a state of polarization to an optical signal transmitted by the optical signal source;
optical splitters;
an optical receiver comprising a power meter that is optically connected, upstream from, the optical fiber under test;
an optical time-domain reflectometer capable of detecting a location of the tight bend in the optical fiber under test; and a storage device capable of storing historical data, wherein the historical data includes data that maps degrees of interference values to at least one of bend radii values, lifetime values, or failure rates of optical fibers;
collect, via the communication interface, test data during the test from the optical receiver;
calculate degrees of interference of a reflected optical signal caused by the tight bend;
correlate the degrees of interference values of the reflected optical signal to at least one of a bend radius value, a lifetime value, or a failure rate value based on the historical data; and
output a test result that includes the at least one of the bend radius value, the lifetime value, or the failure rate value, wherein the optical splitters comprise a first optical splitter and a second optical splitter that are both downstream from the optical fiber under test, and the first optical splitter is configured to receive the reflected optical signal and split the reflected optical signal into two legs, wherein the polarization controllers comprises:
a first polarization controller that is optically connected downstream from the optical fiber under test, and is configured to set a polarization state of one of the legs of the reflected optical signal to be orthogonal or to be aligned with another leg of the reflected optical signal, and wherein the second optical splitter is configured to receive the one of the legs from the first polarization controller and the other leg of the reflected optical signal from the first optical splitter, and the second optical splitter is configured to combine the two legs of the reflected optical signal.

10. The test system of claim 9, wherein, when causing, the one or more processors execute the instructions to:
cause the optical signal source to transmit an optical signal, having a wavelength between the O-band through the U-band, toward the optical fiber under test.

11. The test system of claim 10, wherein the optical splitters comprise a third optical splitter and a fourth optical splitter that are both upstream from the optical fiber under test, and the third optical splitter is configured to receive the optical signal and split the optical signal into two legs, and wherein the polarization controllers comprise:
a second polarization controller that is optically connected upstream from the optical fiber under test, and is configured to set a polarization state of one of the legs of the optical signal to be orthogonal to another leg of the optical signal, and wherein the fourth optical splitter is configured to receive the one of the legs from the second polarization controller and the other leg of the optical signal from the third optical splitter, and the fourth optical splitter is configured to combine the two legs of the optical signal.

12. The test system of claim 9, wherein the other test components are optically connected to each other using a single mode optical fiber.

13. The test system of claim of 9, wherein the parameters include data pertaining to optical characteristics of the optical signal to be transmitted, the type of optical fiber under test, and environmental conditions surrounding the optical fiber under test.

14. The test system of claim 9, further comprising:
an optical isolator optically connected upstream from the optical fiber under test.

15. The test system of claim 9, wherein the optical receiver is optically connected downstream from the second optical splitter and receives the reflected optical signal that includes the combined two legs, and the optical receive measures power values, associated with the reflected optical signal, over time, and wherein the optical receiver calculates degrees of interference based on the measured power values.

16. The test system of claim 9, wherein the test data includes time data indicating times that the reflected optical signal is received by the optical receiver.

17. The test system of claim 9, wherein, when correlating, the one or more processors to execute the instructions to:
compare degrees of interference values to entries in the historical data, wherein each entry includes one or more degrees of interference values; and
determine whether a match occurs between the degrees of interference values and an entry of the historical data; and
select the at least one of the bend radius, the lifetime value, or the failure rate that maps to the entry that includes one or more degrees of interference values that match the degrees of interference values.

18. A method comprising:
storing historical data that includes interference values mapped to at least one of bend radii values, lifetime values, or failure rate values pertaining to at least one of bend insensitive fibers or ultra-bend insensitive fibers;
receiving test parameters that include optical fiber data that identifies an optical fiber under test, wherein the optical fiber under test includes a tight bend;
transmitting an optical signal, via a test system, toward the optical fiber under test, wherein the optical fiber under test is a bend insensitive fiber or an ultra-bend insensitive fiber;
setting a polarization state of the optical signal before the optical signal propagates through the optical fiber under test;
generating a first splitting of a reflected portion of the optical signal, which is caused by the tight bend, into two legs;
setting a polarization state of the reflected portion of the optical signal that has propagated through the optical fiber under test in a manner that causes one or more degrees of interference, wherein setting the polarization state of the reflected portion of the optical signal comprises setting the state of polarization of one of the two legs of the reflected portion of the optical signal to an orthogonal state or an aligned state relative to the other leg of the reflected portion of the optical signal;
measuring instances of power of the reflected portion of the optical signal; and
outputting a result that includes at least one of a bend radius value, a lifetime value, or a failure rate that applies to the optical fiber under test based on the measured instances of power and the historical data.

19. The method of claim 18, further comprising:
generating a second splitting of the optical signal into two legs before setting the polarization state of the optical signal; and
combining legs of the split optical signal, produced by the second splitting, before causing the combined optical signal legs to propagate through the optical fiber under test.

20. The method of claim 18, further comprising:
preventing the reflected optical signal from propagating along a transmit path.

* * * * *